United States Patent [19]

Kensey et al.

[11] Patent Number: 4,749,376
[45] Date of Patent: Jun. 7, 1988

[54] RECIPROCATING WORKING HEAD CATHETER

[75] Inventors: Kenneth Kensey, Hinsdale, Ill.; John Nash, Downingtown, Pa.

[73] Assignee: Intravascular Surgical Instruments, Inc., Frazer, Pa.

[21] Appl. No.: 922,978

[22] Filed: Oct. 24, 1986

[51] Int. Cl.⁴ ............................................. A61B 17/00
[52] U.S. Cl. .................................. 604/22; 128/303 R; 128/305; 128/328
[58] Field of Search .................. 128/305, 751–755, 128/303 R; 604/22; 128/328

[56] References Cited

U.S. PATENT DOCUMENTS

| | | | |
|---|---|---|---|
| 3,565,062 | 2/1971 | Kuris | 128/305 X |
| 3,614,953 | 10/1971 | Moss | 128/305.1 |
| 3,730,185 | 5/1973 | Cook et al. | 128/303 R |
| 4,210,146 | 7/1980 | Banko | 128/305 |
| 4,246,902 | 1/1981 | Martinez | 128/305 X |
| 4,445,509 | 5/1984 | Auth | 128/305 |

FOREIGN PATENT DOCUMENTS

| | | | |
|---|---|---|---|
| 189329 | 7/1986 | European Pat. Off. | 128/328 |
| 191630 | 8/1986 | European Pat. Off. | 128/328 |

Primary Examiner—Michael H. Thaler
Attorney, Agent, or Firm—Caesar, Rivise, Bernstein, Cohen & Pokotilow, Ltd.

[57] ABSTRACT

A catheter device for introduction into the body of a being to effect a procedure, e.g., lumen opening, therein. The catheter is an elongated member having a working head at its distal end and is sufficiently flexible and of small diameter to enable it to be located within the body of the being with the working head at the situs of the procedure. The catheter comprises an elongated drive wire extending through the catheter and motion transtator located at the distal end of the catheter. The wire is rotated at a high speed and the transtator translate that rotary motion into high speed reciprocation of the working head. In some embodiments, the motion transtator also causes the working head to be rotated at the same time it is reciprocated. In other embodiments, the working head is only reciprocated. In all cases, the motion of the working head is at a very high speed. The catheter also includes means to provide a fluid therethrough so that when the catheter is used to open a lumen, e.g., an arterial restriction caused by atherosclerotic plaque, the rotation of the working head causes the fluid to impact the artery wall.

8 Claims, 4 Drawing Sheets

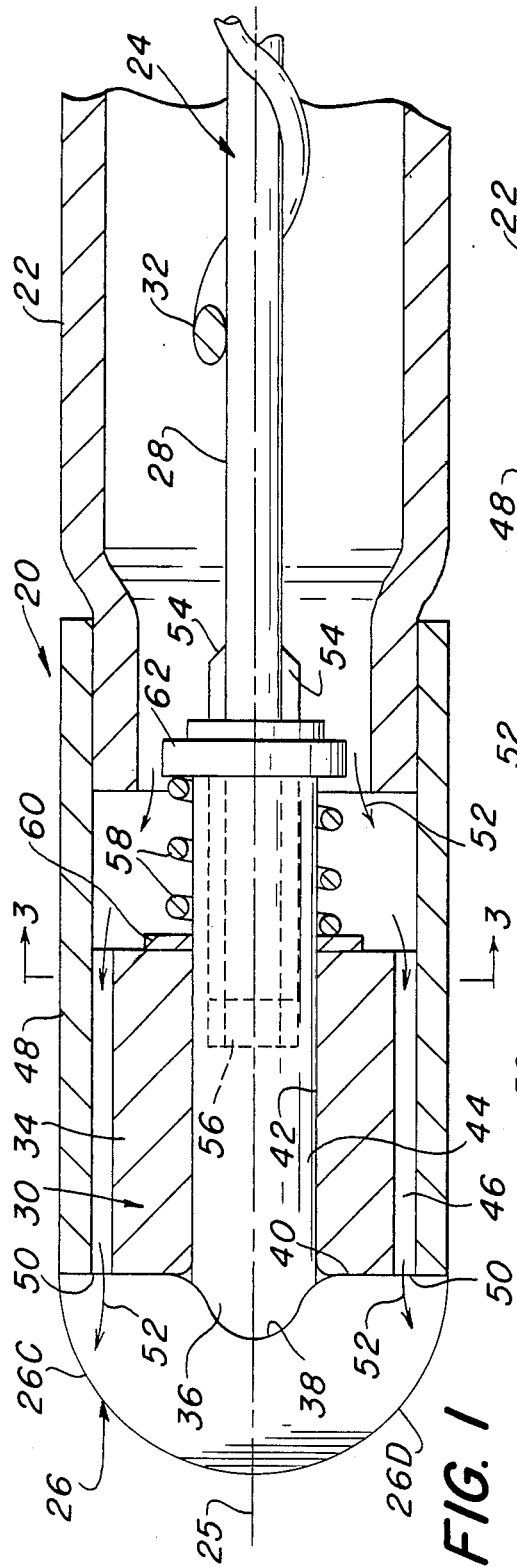
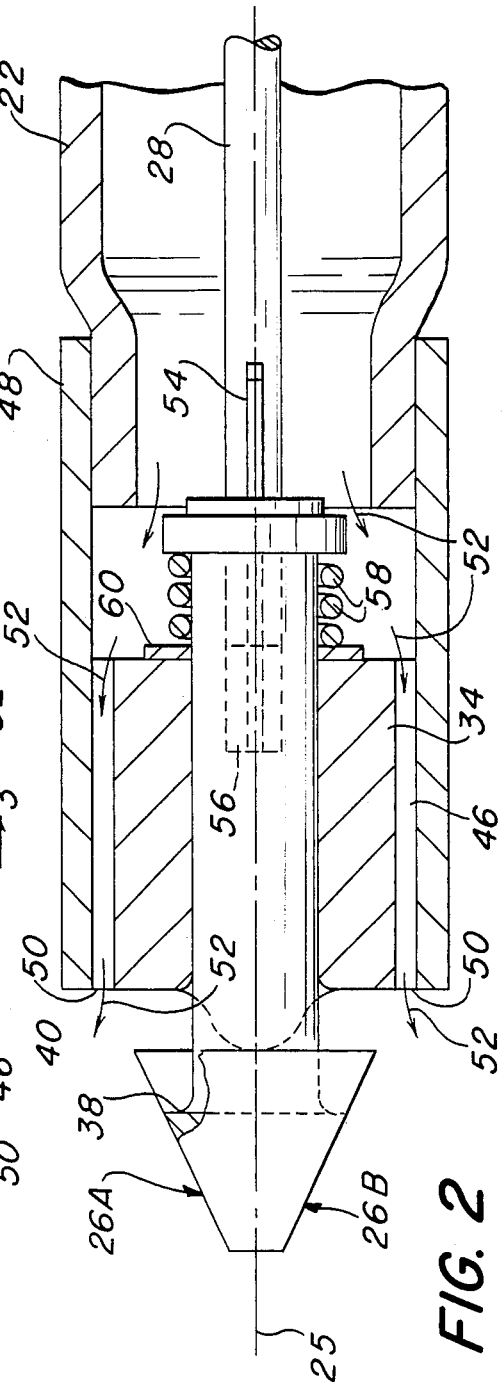
FIG. 1
FIG. 2

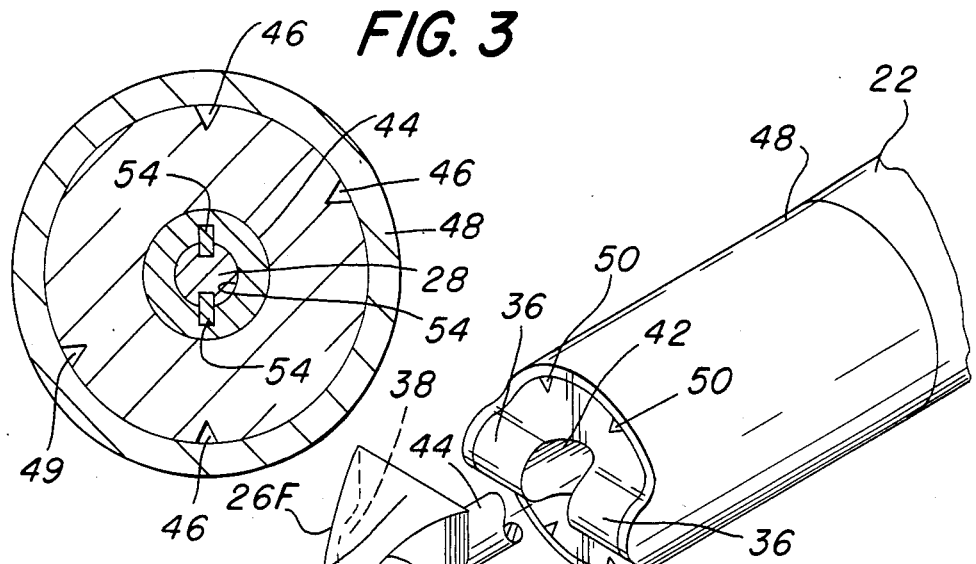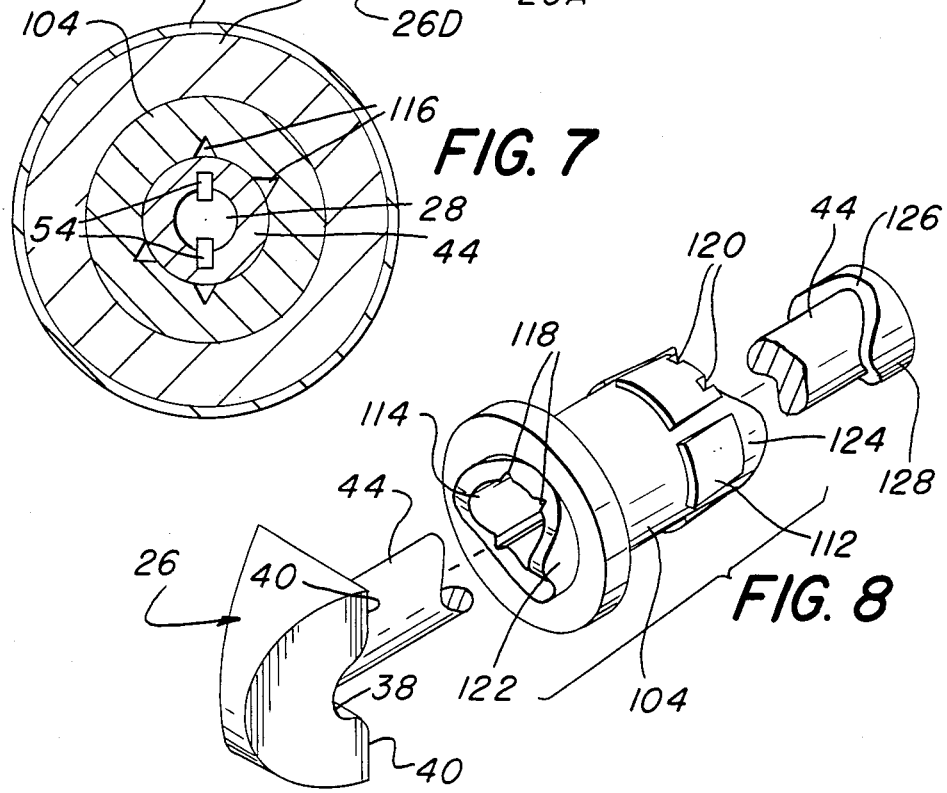

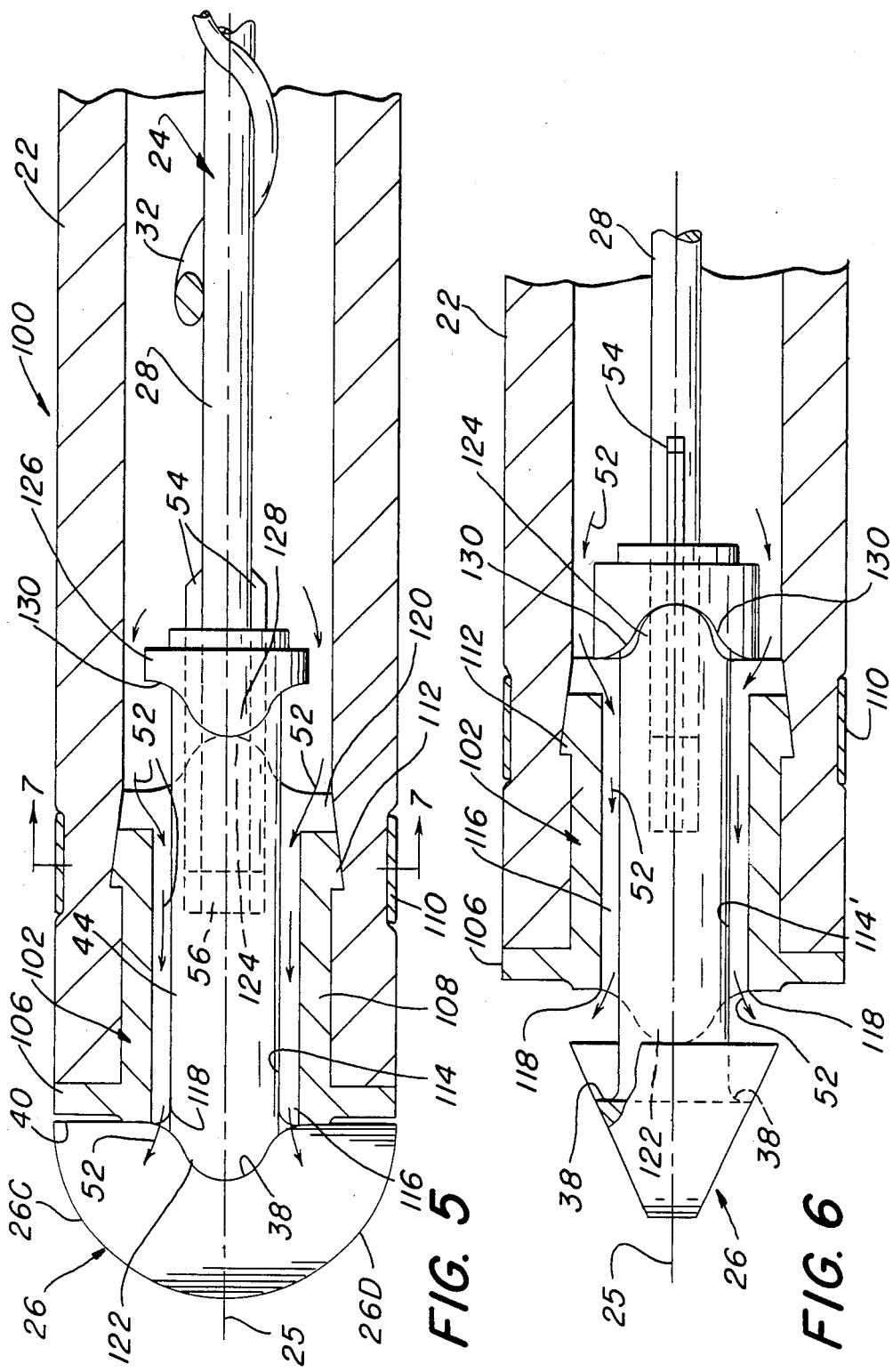

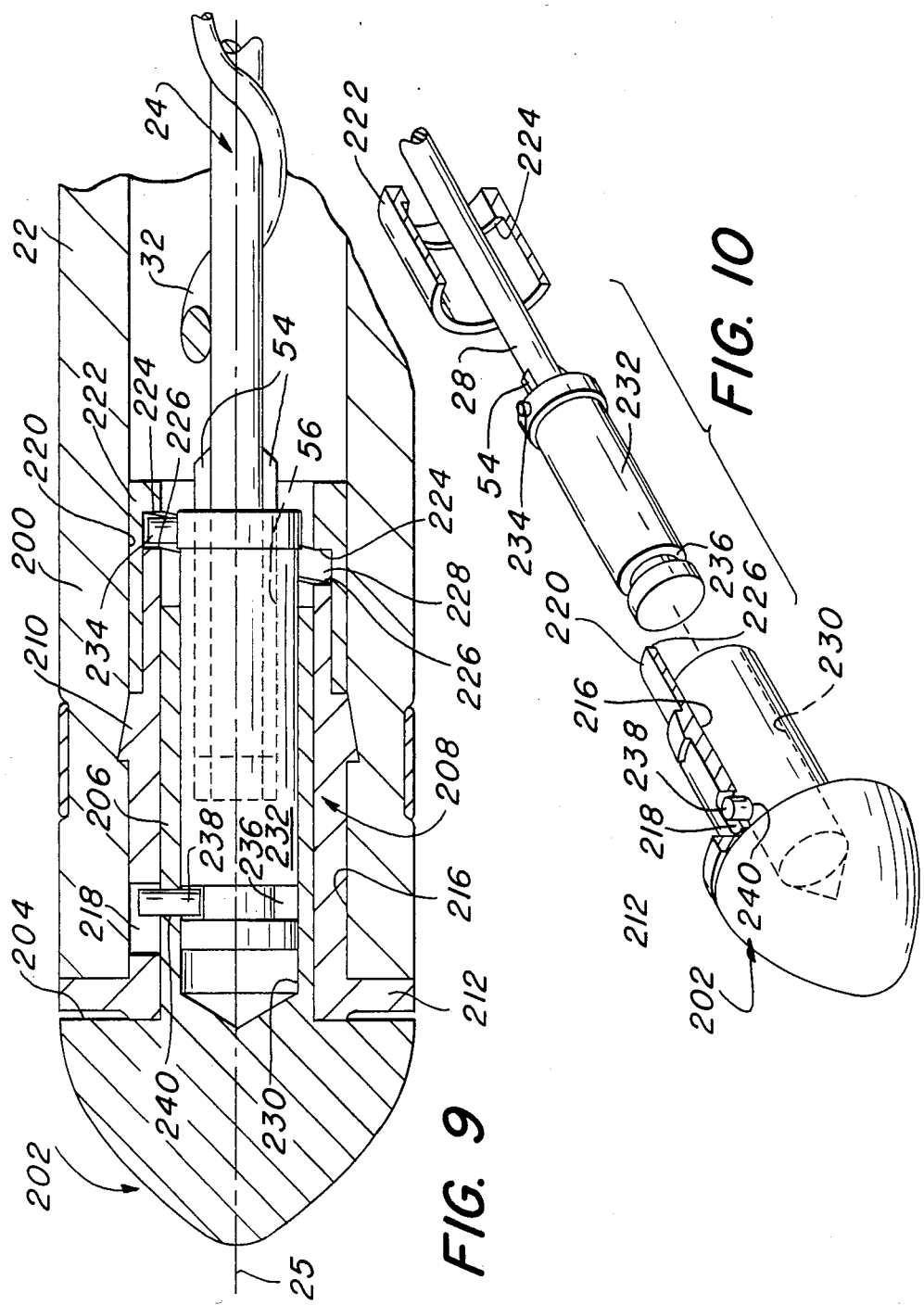

RECIPROCATING WORKING HEAD CATHETER

BACKGROUND OF THE INVENTION

This invention relates generally to medical devices and more particularly to flexible, power-driven catheters for intravascular surgery and other surgical and in-body medical procedures.

Various types of catheter instruments have been suggested or disclosed for effecting non-invasive or minimally invasive surgical or medical procedures within the body of a person or animal. For example, in U.S. Pat. No. 4,445,509 (Auth) there is disclosed a recanalization catheter designed specifically for cutting away hard, abnormal deposits, such as atherosclerotic plaque, from the inside of an artery, and while supposedly preserving the soft arterial tissue. That recanalization catheter includes a sharp edged, multi-fluted, rotating cutting tip mounted at the distal end of the catheter and arranged to be rotated by a flexible drive shaft extending down the center of the catheter. The rotation of the cutting head is stated as producing a "differential cutting" effect, whereupon relatively hard deposits are cut away from relatively soft tissue. Suction ports are provided in the cutting tip to pull the hard particles produced by the cutting action into the catheter for removal at the proximal end thereof so that such particles do not flow distally of the catheter where they could have an adverse effect on the patient's body.

It has been determined that the use of sharp rotary cutting blades in a revascularization catheter can have various adverse effects on arterial tissue, e.g., snagging, cutting or otherwise damaging the tissue of the artery wall.

In our copending U.S. patent application Ser. No. 914,954, filed on Oct. 3, 1986, entitled Catheter Based Surgical Methods and Apparatus Therefor, assigned to the same assignee as this invention, and whose disclosure is incorporated by reference herein, there is disclosed and claimed catheters and methods of use for effecting a surgical procedure, such as opening an atherosclerotic restriction in an artery, or opening a fallopian tube, destroying or pulverizing a stone in a bodily lumen, etc., at a remote location within the body. The catheters of that invention consist of elongated flexible members of sufficient flexibility and small diameter to enable them to be readily passed through the body of the patient, e.g., through a portion of the vascular system, to the situs of the procedure to be accomplished, e.g., the location of the atherosclerotic plaque in the artery. Those catheters include at their distal end a working head arranged for high speed movement, e.g., rotation, to effect the procedure and without posing any danger to contiguous bodily tissue. In some embodiments, the catheter may eject fluid at the working head to expedite the procedure.

In another of our copending U.S. patent applications, that is, U.S. application Ser. No. 921,973, filed on Oct. 22, 1986, entitled Catheter With High Speed Moving Working Head, assigned to the same assignee as the subject invention, and whose disclosure is incorporated by reference herein, there is disclosed and claimed catheters, their working heads and methods of use for effecting surgical procedures at a remote location within the lumen of the body. Those catheters include rotary working heads having non-sharp impacting surfaces to effect material removal without cutting. The catheters are arranged to eject fluid adjacent the working head to expedite the procedure. When such catheters are used for treating atherosclerotic disease by recanalizing arteries, the catheter is guided through the vascular system of the patient to the site of the vascular occlusion or blockage that has been determined to exist so that the rotary working head is located immediately adjacent the restriction. The working head is then rotated about the longitudinal axis of the catheter at a high rate of speed, e.g., from 10,000 rpm to 200,000 rpm. At the same time, fluid is passed through the catheter and out of its distal end adjacent the working head. The opening of the restriction to allow freer flow of blood is effected by the dilation and/or selective emulsification properties of the catheter's working head. In this connection, during the rotation of the working head fluid jets exiting the distal end of the catheter at the working head are immediately accelerated laterally by portions of the working head so that they are broken up into small segments that develop considerable momentum as they are flung out in all directions, including radial directions, toward the wall of the artery. These liquid segments transfer their momentum to the artery wall, forcing the artery wall outward laterally in all directions, thereby aiding in dilating it.

The rotating working head, with its non-sharp impacting surfaces also serves to differentiate atherosclerotic tissue from normal tissue through the inherent differences in the tissues' physical properties and organizational patterns. Therefore, when the catheter is passed translumenally through a diseased artery, its working head serves to emulsify occlusive lesions not covered with fibrous plaque by repeatedly impacting the material forming the restriction as the working head is rotated, and with minimal risk of puncture or perforation of the contiguous arterial wall. The emulsification process is accomplished by the repeated impaction of the non-sharp impacting surfaces on the materials forming the restriction. This action causes the material to be broken away in small particles. The rotation of the working head also produces a powerful vortex flow at the working head so that any particles produced by the impacting action are drawn back into contact with the impacting surfaces of the rotating working head. Accordingly, those particles are repeatedly impacted over and over, with each impaction reducing the size of the particles further until the resulting particle size is sufficiently small that they can be permitted to flow to downstream tissue without causing any significant deleterious effects to the patient.

For some surgical or other in-body medical applications reciprocatory action of a working head, in conjunction with either rotary motion thereof or alone, may prove beneficial or more effective than pure rotary motion.

OBJECTS OF THE INVENTION

Accordingly, it is the general object of the instant invention to provide catheters which overcome the disadvantages of the prior art.

It is a further object of the instant invention to provide catheters having working heads which are arranged for high speed reciprocation to effect a surgical or medical procedure within the body of a being and without damaging adjacent tissue.

It is still a further object of the instant invention to provide catheters having working heads which are arranged for high speed reciprocation and rotation to effect a surgical or medical procedure within the body of a being and without damaging adjacent tissue.

It is still a further object of the instant invention to provide catheters for intralumenal use to effect the dilation of the lumen without damaging the tissue thereof.

It is yet a further object of the instant invention to provide catheters for use in opening restrictions formed of an undesirable material in a portion of a lumen by dilating the lumen and/or removing some of said undesirable material, allowing it to flow distally, all without resulting in injury to the patient.

SUMMARY OF THE INVENTION

These and other objects of the instant invention are achieved by providing a catheter for introduction into the body of a being to effect a procedure therein. The catheter includes a distal end and comprises an elongated flexible member of sufficient flexibility and small diameter to enable it to be located within said body with its distal end located at the situs for said procedure. The catheter comprises a working head located adjacent the distal end and drive means therefor. The drive means is arranged to effect a high speed reciprocation or reciprocation and rotation of the working head.

DESCRIPTION OF THE DRAWING

Other objects and many of the attendant advantages of this invention will become readily appreciated when the same becomes better understood by reference to the following detailed description when considered in connection with the accompanying drawing wherein:

FIG. 1 is a side elevational view, partially in section, showing the distal end of a rotary/reciprocating working head catheter of the subject invention and with the catheter's working head shown at one end of its rotary/reciprocatory travel path;

FIG. 2 is a view similar to that of FIG. 1 but showing the working head at the other end of its rotary/reciprocatory travel path;

FIG. 3 is a sectional view taken along Line 3—3 of FIG. 1;

FIG. 4 is a reduced, exploded perspective view of the distal end of the catheter shown in FIG. 1;

FIG. 5 is a view similar to that in FIG. 1 but showing an alternative embodiment of a rotary/reciprocating working head catheter of this invention and with the catheter's working head shown at one end of its rotary/reciprocatory travel path;

FIG. 6 is a view similar to that of FIG. 5 but showing the working head at the other end of its rotary/reciprocatory travel path;

FIG. 7 is a sectional view taken along Line 7—7 of FIG. 5;

FIG. 8 is a reduced, exploded perspective view of the distal end of the catheter shown in FIG. 5;

FIG. 9 is a sectional view of a distal end of a reciprocating working head catheter of the subject invention and with the catheter's working head shown at one end of its reciprocating travel path; and FIG. 10 is a reduced, exploded perspective view of the distal end of the catheter shown in FIG. 9.

DETAILED DESCRIPTION OF THE PREFERRED EMBODIMENT

Referring now in greater detail to the various figures of the drawing wherein like reference characters refer to like parts, there is shown in FIG. 1 the distal end of a catheter 20 for intravascular or other in-body surgical or medical applications. The catheter 20 basically comprises an elongated flexible tubular body member or jacket 22 having a drive system 24 (to be described later) located therein and a moveable working head 26 located at its distal end.

The jacket 22 is formed of a suitable material, e.g., plastic, and has a small outside diameter. In a preferred embodiment shown herein the outside diameter is approximately 1.5 mm (5 French) or less. This size catheter is merely exemplary. Thus, in accordance with this invention, the catheter can be constructed as small as 2 French (0.6 mm).

Located within the hollow interior of the catheter tube 22 is the drive system 24 (only a portion of which can be seen in FIG. 1). The drive system is a flexible one which is preferably constructed in accordance with the teachings of our copending U.S. patent application Ser. No. 746,220, filed on June 19, 1985, now U.S. Pat. No. 4,686,982 entitled Spiral Wire Bearing for Rotating Wire Drive Catheter, assigned to the same assignee as this application and whose disclosure is incorporated by reference herein. That drive assembly is arranged to cooperate with translation means 30 located within the distal end of the catheter (and to be described later) to effect the high speed movement, e.g., rotation and reciprocation, of the working head 26. Thus, the drive assembly 24 basically comprises an elongated multistrand drive cable 28 or drive wire which extends down the central axis 25 of the catheter within the catheter jacket 22 from a proximal point (located outside of the body of the patient) to the motion translation means 30. The cable is arranged to be rotated at a high speed about axis 25 to effect the high speed rotation/reciprocation of the working head 26. To that end, the motion translation means converts the high speed rotation of the drive cable 28 into rotary/reciprocating motion of the working head 26.

As disclosed in our aforementioned copending patent application Ser. No. 746,220, the drive cable 28 is supported in the central position within catheter 22 and along axis 25 by means of a spiral bearing 32. The bearing 32 basically comprises a helical or spiral cylindrical coil of wire surrounding the drive cable 28. The spiral bearing 32 extends substantially the entire length of the catheter from a proximately located point adjacent located outside the body of the patient to the distal end of the catheter. The inside diameter of the central passageway extending down bearing coil 32 is slightly greater than the outside diameter of the drive cable 28 so that the cable can freely rotate therein.

It should be pointed out at this juncture, that the drive cable 28 can, if desired, be drawn or swaged so that its outer periphery has a greater contact surface area with the spiral bearing than if the cable were unswaged. This feature is shown and claimed in our copending U.S. patent application Ser. No. 938,698, filed on Dec. 5, 1986, and entitled Catheter With Means to Prevent Wear Debris from Exiting. Also disclosed and claimed in that application is a spiral wire bearing whose inner surface, that is, the surface defining the central passageway therethrough, is substantially planar in order to further increase the engaging surface area. A bearing constructed in accordance with that feature can, if desired, be used to support the drive cable 28 herein. The drive cable 28 is arranged to be connected via coupling means (not shown) at its proximal end to a motor (not shown), such as an electric motor, to effect its rotation about axis 25. In particular, the drive cable 28 is arranged to be rotated at a high rate of speed, e.g., from 10,000 rpm to 200,000 rpm or greater, by the motor even if the catheter is bent through a small radius of curvature, e.g., 0.75 inches (1.9 cm) in its placement within the body, and without the creation of any standing waves which could result in unwanted vibration to the catheter.

The spacing between the convulusions of the spiral wire bearing, the inner surface of the catheter tube 22 and the outer surface of the drive cable form a passageway through the catheter through which a fluid (e.g., liquid) can flow from the proximal end of the catheter to the distal end. This liquid can be utilized to cool or lubricate the bearing system as well as the working head tissue interface. Moreover, as will be described in detail later, the liquid is expelled at the working head to aid in the procedure carried out by the working head, e.g., the dilation of arterial tissue. Further still, the liquid which is passed down the catheter can, if desired, be oxygenated to eliminate distal ischemia when the catheter is used for arterial restriction opening procedures. Also, if desired, nitrates, contrast media or other drugs can be added to the liquid as needed during the procedure.

The details of the outer surface of the working head 26 will now be discussed briefly. Thus, the working head is preferably constructed in accordance with the teachings of our aforenoted copending application Ser. No. 921,973, entitled Catheter with High Speed Moving Working Head. In particular, as can be seen in FIGS. 1, 2 and 4, the outer surface of the working head 26 is of convex hemispherical shape and having a pair of planar diametrically opposed relieved surfaces 26A and 26B. The section of the spherical surface between the relieved surfaces 26A and 26B defines a pair of cam surfaces 26C and 26D. The interface of each of the cam surfaces 26C and 26D with the associated relieved surfaces 26A and 26B is rounded or radiused so that each interface surface is not sharp (although in the scale of the drawings herein it may appear to be a sharp line). These rounded or radiused surfaces form non-sharp, impacting surfaces for the working head. Thus, as described in detail in our aformentioned copending patent application, upon the rotation of the working head 26 about axis 25, the non-sharp impacting surfaces make contact with the atherosclerotic tissue to effect its emulsification by differentiating the diseased tissue from the relatively undiseased tissue. Moreover, as will be described later, the rotation of the working head 26 about axis 25 causes fluid exiting the catheter at the distal end thereof (an operation to be described later) to be broken into segments or slugs and thrown in a generally hemispherical pattern about the rotating/reciprocating head 26 by the relieved surfaces 26A and 26B. The exiting liquid slugs, most of which have some radial directional component, develop tremendous momentum as they are flung outward toward the artery wall so that their momentum is transferred to the artery wall, thereby aiding in forcing the artery wall outward in all radial directions. This action helps to effectively dilate the artery.

Moreover, the radial pressure developed by the rotating working head is substantial and can raise local static pressure immediately adjacent the working head by approximately 100 to 200 mm of Hg. This increased pressure on the artery wall contiguous with the rotating working head is not due solely to the impact of the liquid slugs thereon, but is also due to recirculation of the liquid surrounding the working head. In this connection, as described more fully in our aforenoted copending application, the rotation of the working head about axis 25 produces a powerful, toroidal shaped vortex contiguous with the working head. This vortex, in addition to augmenting the application of increased pressure to the artery wall contiguous with the working head, also has the effect of recirculating any particles that may have been broken off from the material forming the arterial restriction by the impact of the rotating working head with that material. Thus, if the material forming the restriction is such that particles are broken away, they are circulated by the vortex and carried back into the rotating working head 26 where they are progressively reduced in size. This progressive size reduction action has the effect of producing particles which are sufficiently small, e.g., 95% have a surface area less than that of a red blood cell, so that they may be enabled to flow distally without substantial deleterious effects to the patient.

As can be seen clearly in FIG. 1, the translation means 30 includes a journal bearing 34 having a pair of diametrically opposed cam lobes 36 projecting from the distal end thereof (see FIG. 4). The working head 26 includes a correspondingly shaped pair of cam recesses 38 in the rear face thereof and which are arranged to cooperate (receive) the cam lobes 36 when the working head is in the rotational position shown in FIG. 1. The remaining portion of the rear face of the working head 26 between the cam recesses 38 is flat and denoted by the reference numeral 40. The cam recesses and flatted surfaces on the rear of the working head also form a part of the translation means 30.

The journal bearing 34 also includes a longitudinally extending bore 42 coaxial with axis 25 and arranged to receive therein the axle 44 of the working head. That axle is fixedly secured to the rear (proximal end) of the working head. Four generally V-shaped grooves 46 extend down the outer periphery of the journal bearing 34 from the proximal end thereof to the distal end and parallel to the longitudinal axis 25. The journal bearing is held in place by a tubular sleeve 48 tightly fitting about the periphery of the journal bearing. The sleeve 48 covers the grooves 46 along their length so that the grooves 46 become longitudinally extending passageways. As can be seen in FIG. 4, the distal end of the sleeve 48 is flush with the distal end of the journal bearing. The proximal end of the sleeve 48 serves to trap the distal end of the catheter jacket 22 therein to secure the journal bearing to the catheter jacket.

With the bearing 34 in position as just described fluid flowing through the interior of the catheter jacket 22 is enabled to flow into the passageways 46 at the proximal end of the journal bearing and out through exit ports 50 at the distal end of each of the passageways. The direction of fluid flow through the catheter is denoted by the arrows bearing the reference numeral 52.

As can be seen clearly in FIGS. 1 and 2, the distal end of the drive cable 28 includes four elongated splines 54 extending parallel to longitudinal axis 25 and equidistantly spaced about the periphery of the distal end of cable 28. The proximal end of the working head's axle 44 includes a centrally located bore 56 adapted to receive the splined distal end of the cable 28. To that end, the bore 56 includes a central cylindrical opening and four longitudinally extending projecting slots, each adapted for receipt of a respective spline 54 therein. As will be appreciated by those skilled in the art, the distal end 28 of the cable with the splines is enabled to slide within the bore 56 along axis 25 so that when cable 28 is rotated about axis 25 it rotates the working head 26 about that axis while the working head reciprocates therealong and without reciprocation of the drive cable 28.

A helical compression spring 58 is disposed about the outer periphery of the axle 44 and trapped between an annular thrust pad 60 disposed on the proximal end of the journal bearing and a collar 62 fixedly secured to the proximal end of the working head axle 44.

The rotation of drive cable 28 causes the concommitant rotation of axle 44 (and hence working head 26) about axis 25 in such a manner that the cam lobes 36 are scanned by the rotating cam recesses 38 and interposed flats 40. Therefore when the lobes 36 engage the flats 40 the working head 26 is slid along axis 25 to the "extended" position shown in FIG. 2, and when the lobes 36 are disposed within recesses 38, the working head is slid along axis 25 to the "retracted" position shown in FIG. 1. Thus, the working head 26 is enabled to rotate and reciprocate at the same time via the cooperation of the cam lobes, cam recesses, flats and the spring, with the splined bore 56 cooperating with the splined end of the drive cable to enable the working head to move to and fro along axis 25 without such concommitant movement of the drive cable. The compression spring 58 serves to move the working head from the extended position shown in FIG. 2 back to the retracted position shown in FIG. 1 during each cycle of reciprocation.

The details of an alternative rotary/reciprocation catheter will now be described with reference to FIGS. 5-8. Thus, the catheter shown therein is denoted by the reference numeral 100 and includes a number of component parts which are identical or similar in construction to those of catheter 20. Accordingly, all such common or similar parts will be denoted by the same reference numerals. Furthermore, in the interest of brevity, the details of the structure and operation of those common components will not be reiterated.

As can be seen, the catheter 100 basically comprises the tubular jacket 22 and through which the rotary drive assembly 24 extends. Located at the distal end of catheter 100 is a rotary working head 26 whose construction is similar to the working head of like number in embodiment 20 except that the proximal end of its axle 44 is constructed differently. That alternative axle construction will be considered later. Catheter 100 also includes motion translating means 102 located at the distal end of the catheter and adapted to convert the rotary motion of the drive cable 28 into rotary/reciprocating motion of the working head 26. The translation means 102 basically comprises a journal bearing 104. The bearing 104 includes a flanged end face 106 arranged to abut the distal end of the catheter's jacket 22 and a tubular central portion 108. The outside diameter of tubular portion 108 is approximately that of the inside diameter of the catheter jacket 22 so that it is snuggly fit therein. The journal bearing is held firmly in place by a retaining band 110 which tightly encircles the periphery of the catheter jacket 22 so that plural gripping teeth 112 located about the periphery of the tubular portion 108 dig into the interior surface of the catheter jacket to hold the bearing in place therein. The bearing 104 also includes a central bore 114 extending therethrough and aligned with the longitudinal central axis 25 of the catheter.

Extending down the central bore 114 of the bearing 104 are four, equidistantly spaced, V-shaped grooves 116. The distal end of each groove 116 terminates at a respective fluid exit port 118 located at the front face of the distal end flange 106, while the proximal end of each groove 116 terminates in a respective, generally radially extending, relief groove 120.

The fluid flowing down the interior of the catheter jacket 22 flows into the relief grooves 120, through associated grooves 116 and out of the ports 118 at the end face of the bearing and adjacent to the longitudinal axis 25. The direction of liquid flow is denoted by the arrows bearing the reference numeral 52.

The distal end of bearing 104 includes a pair of diametrically opposed projecting cam lobes 122. The cam lobes 122 are similar in construction to the cam lobes 36 described with reference to the catheter 20 and are arranged to cooperate with cam recesses 38 and flatted surfaces 40 on the rear face of the working head 26 in a manner similar to that as described with reference to the catheter 20. The proximal end of journal bearing 104 also includes a pair of cam lobes 124. The cam lobes of this second pair are also diametrically opposed to each other and are axially aligned with the cam lobes 122 at the distal end of the bearing.

The proximal end of axle 44 of the cutting head 26 of catheter 100 is different than that of catheter 20. In this connection, the proximal end of axle 44 of catheter 100 includes an annular collar 126 of larger diameter than that of the axle itself. The collar 126 includes a pair of diametrically opposed cam lobes 128 projecting towards the working head. The cam lobes 128 are axially aligned with the cam lobes 124 on the proximal end of the bearing 104. The collar's surfaces between its cam lobes 128 are in the form of interposed cam recesses 130. The cam lobes, recesses and flatted surfaces all form portions of the motion translation means 102.

The working head 26 of catheter 100 like that of catheter 20 includes an axial, splined bore 56 into which the distal end of the drive cable 28 with its splines 54 is disposed.

Therefore, as will be appreciated by those skilled in the art, as the drive cable 28 is rotated about axis 25, its rotary motion is coupled to the working head's axle 44, via the splines 54, whereupon the working head is rotated about axis 25. Since the collar 126 with its cam lobes 128 is fixed to axle 44 it rotates in unison with the axially aligned recesses 38 at the rear of the working head 26. The cam recesses 38 on the working head and the cam projections 128 on the collar 126 are syncronized so that they engage the two aligned cam projections 122 and 124 on the opposite ends of the bearing 104. Accordingly, the working head is reciprocated back and forth between the positions shown in FIGS. 5 and 6 by the engaging cam surfaces as the working head is rotated about axis 25 by drive cable 28 and without the need for any spring like that utilized in the embodiment of catheter 20.

The fluid 52 exiting through the ports 118 is accelerated in the hemispherical pattern as described with reference to catheter 20 and will thus not be described further.

The combination of reciprocating and rotary motion produced by the working head 26 of the catheters 20 and 100 when used in treating atherosclerotic disease appears to be beneficial to cause the working head to seek a path and stretch the tissue.

In some applications, such as where very delicate tissue is involved, it is desirable that the working head only be reciprocated, and not rotated, and with the velocity of the reciprocation being reduced to a small amplitude. In FIGS. 9 and 10 there is shown the distal end of an alternative catheter 200 having a purely reciprocating working head. In the interest of brevity, all similar or identical parts to those previously described will be given the same reference numerals in catheter 200 and their structural details and operation will not be reiterated.

Thus, as can be seen, catheter 200 basically comprises the heretofore identified catheter jacket 22 and the rotary drive system 24. The working head is different than in catheters 20 and 100 and is hence denoted by the reference numeral 202. As can be seen in FIG. 10, the working head 202 basically comprises a generally conically-shaped member having a rounded tip contiguous with the central axis 25 of the catheter and a gradually arcuate outer surface adjacent the planar rear face 204 of the tip. Projecting from the rear face 204 is a unitary cylindrical axle 206.

Disposed within the distal end of catheter jacket 22 is rotary-to-reciprocating translation means 208. The translation means 208 basically comprise a journal bearing 210 having a flanged distal end 212, arranged to abut the end of the catheter's jacket 22, and a tubular portion 214. The outside diameter of the tubular portion 214 is approximately that of the inside diameter of the catheter jacket 22 so that it is held snuggly in place therein. A retaining band and gripping teeth, like that described with reference to catheter 100 is used to hold the journal bearing 210 in place.

A bearing 210 also includes a central bore 216 extending therethrough and aligned with the longitudinal central axis 25 of the catheter. A short length longitudinally extending slot 218 is provided in the portion 214 of the bearing 210. The proximal end of the bearing 210 includes an annular peripheral ledge 220. A cap 222 whose outside diameter is the same as the maximum outside diameter of the tubular portion of bearing 210 is disposed within the annular recess 220. The cap 222 includes a continuous cam surface 224 which is inclined in a direction along longitudinal axis 25. The distal end of the bearing 210 also includes a continuous cam surface 226 which extends parallel to cam surface 224 so that the space between the surfaces 224 and 226 forms an inclined cam raceway 228. The raceway extends at an acute angle to axis 25 so that one point in the raceway is disposed closest to the distal end of the catheter and the diametrically opposite point in the raceway is disposed furthest from the distal end of the catheter.

The axle 206 of the working head 202 includes a bore 230 extending therein from the proximal end of the axle to a point adjacent the tip of the head and is axially aligned with central axis 25. A cylindrically-shaped coupling 232 is disposed within the bore 230. The coupling is arranged to rotate freely within bore 230 about axis 25 but not to slide therealong. The coupling 232 includes a splined bore 56 like that described with reference to catheters 20 and 100 and which is coaxial with the axis 25. The bore 56 is adapted to receive therein the splined distal end of drive cable 28 in the same manner as described heretofore. The proximal end of the coupling 232 includes a pin 234 projecting radially outward therefrom and so that its free end is located within the cam raceway 228. The distal end of the coupling 232 includes an annular groove 236 extending about its periphery. A pin 238 extends through and is fixedly secured in a radial hole 240 in the working head's axle 206. The radially inward free end of pin 238 is located within annular groove 236 in the coupling 232, while its radially outward free end is located within the longitudinally extending slot 218 in the bearing.

As will be appreciated by those skilled in the art, operation of the catheter 200 is as follows: upon rotation of the drive cable 28 the coupling 232 is rotated concommitantly therewith about axis 25. Accordingly, the free end of pin 234 slides along the continuous cam raceway 228. This action causes the coupling 232 to not only rotate about axis 25 but also to reciprocate therealong with the extend of travel being defined by the inclination angle of the raceway. However, only the reciprocatory motion of the coupling 232 is passed to the working head. In this regard, the pin 238 prevents the coupling from sliding along axis 25 with respect to the working head. The pin does allow the working head to reciprocate with respect to the bearing, however. In this connection, the pin 238 is restrained in slot 218 so that it can reciprocate therealong but is prevented from rotating about axis 25. Accordingly, the rotation of the drive cable 28 effects only reciprocation of the working head 202.

It should be pointed out at this juncture, that the reciprocating and/or reciprocating/rotating working heads of the subject invention can also be operated at much high speeds (frequency) than described heretofore to impart ultrasonic vibratory energy to the situs of the in-body procedure in order to further effectuate that procedure.

As will be appreciated by those skilled in the art, in the reciprocating/rotating embodiments of this invention, the frequency of reciprocation can be multiplied by utilizing multi-lobe cams. In this regard, doubling the number of lobes doubles the frequency of oscillation. Moreover, the extent of travel can be adjusted by appropriate configuration of the engaging cam surfaces. In the purely reciprocating embodiments of this invention the extent of travel can be adjusted as desired by appropriate configuration of the cam raceway.

Without further elaboration, the foregoing will so fully illustrate our invention that others may, by applying current or future knowledge, readily adopt the same for use under various conditions of service.

We claim:

1. A device for introduction into the body of a being to effect a procedure therein, said device being an elongated flexible catheter having a distal end, said catheter having a longitudinal axis and being of sufficient flexiblity and small diameter to enable it to be readily located within said body with its distal end located at the situs for said procedure, said catheter comprising a working head located adjacent the distal end and drive means therefor, said drive means comprising at least one elongated member extending down said catheter and arranged to be rotated at a high rate of speed about said axis and motion translating means located adjacent said distal end of said catheter and coupled to said elongated member and said working head for converting said rotary motion of said elongated member into reciprocating motion back and forth in a direction parallel to sadi axis, whereupon said working head is reciprocated at a high speed back and forth in a direction parallel to said axis.

2. The catheter of claim 1 wherein said working head is also rotated about said axis by said drive means.

3. The catheter of claim 2 wherein said working head is arranged to be rotated at a speed in excess of 20,000 rpm.

4. The catheter of claim 1 wherein said motion translating means comprises at least one cam surface.

5. The catheter of claim 4 wherein said working head comprises one cam surface and said motion translating means comprises another cam surface, said two cam surfaces cooperating with one another to translate said rotary motion into said reciprocating motion.

6. The catheter of claim 1 wherein said working head comprises at least one, non-sharp impacting surface arranged to repeatedly impact some bodily material located at the situs of said procedure.

7. The catheter of claim 6 wherein means are provided to pass a fluid through said catheter to said working head and wherein said working head is arranged to cause at least a portion of said fluid to be directed away therefrom in directions having at least some radial component.

8. The catheter of claim 1 wherein said elongated member comprises at least one wire.

* * * * *